United States Patent

Harris et al.

[11] Patent Number: 4,758,570
[45] Date of Patent: Jul. 19, 1988

[54] PESTICIDAL NITROMETHYLENE DERIVATIVES

[75] Inventors: Martin Harris, Sittingbourne; Michael Pearson, Teynham, both of England

[73] Assignee: E. I. DuPont de Nemours and Company, Wilmington, Del.

[21] Appl. No.: 49,953

[22] Filed: May 15, 1987

[30] Foreign Application Priority Data

May 20, 1986 [GB] United Kingdom ............... 8612238

[51] Int. Cl.$^4$ .................. A61K 31/505; C07D 239/06
[52] U.S. Cl. ..................................... 514/256; 544/335
[58] Field of Search ......................... 544/335; 514/256

[56] References Cited

U.S. PATENT DOCUMENTS 3,969,354  7/1976  Tieman et al. ................ 544/335
4,590,272  5/1986  Shiokawa et al. ............. 544/335
4,647,570  3/1987  Shiokawa et al. ............. 544/335

Primary Examiner—Glennon H. Hollrah
Assistant Examiner—James H. Turnipseed

[57] ABSTRACT

The invention provides 2-nitromethylene hexahydropyrimidines of the general formula:

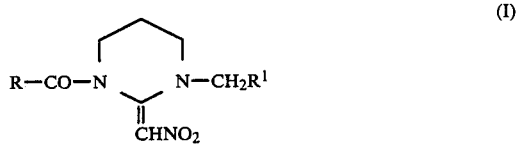

in which R represents a hydrogen atom; a cycloalkyl group optionally substituted by alkyl and/or halogen; or a group of formula —(CO)$_n$(Y)$_m$R$^2$ in which n is 0 or 1, Y is oxygen or sulphur, m is 0 or 1 and R$^2$ represents an alkyl, alkenyl or alkynyl group optionally substituted by one or more substituents selected from halogen; alkoxy; haloalkoxy; alkoxyalkoxy; hydroxy; acyloxy; thiol; cycloalkyl optionally substituted by alkyl and/or halogen; and optionally substituted phenyl; and R$^1$ represents an optionally substituted phenyl group; their preparation and their use as pesticides.

10 Claims, No Drawings

PESTICIDAL NITROMETHYLENE DERIVATIVES

This invention relates to certain 2-nitromethylene-hexahydropyrimidines, to processes for their preparation and to their use as pesticides, in particular against insect pests.

European Patent Application No. EP-A-136636 (Nihon Tokushu Noyaku Seizo K.K.) discloses 1-halobenzyl-2-nitromethylene-hexahydropyrimidines having activity as insecticides, miticides, tickicides and nematicides.

It has now been found that certain 1-acyl-3-benzyl-2-nitromethylene hexahydropyrimidines exhibit interesting pesticidal activity.

Accordingly the invention provides a 2-nitromethylene hexahydropyrimidine compound of the general formula:

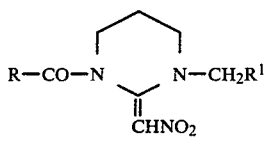 (I)

in which R represents a hydrogen atom; a cycloalkyl group optionally substituted by alkyl and/or halogen; or a group of formula $-(CO)_n(Y)_mR^2$ in which n is 0 or 1, Y is oxygen or sulphur, m is 0 or 1 and $R^2$ represents an alkyl, alkenyl or alkynyl group optionally substituted by one or more substituents selected from halogen; alkoxy; haloalkoxy; alkoxyalkoxy; hydroxy; alkanoyloxy; thiol; cycloalkyl optionally substituted by alkyl and/or halogen; and optionally substituted phenyl; and $R^1$ represents an optionally substituted phenyl group.

Preferred cycloalkyl groups have 3 to 6 ring carbon atoms. In an optionally substituted phenyl group, the optional substituents are preferably selected from halogen atoms and alkyl, alkoxy, haloalkyl, haloalkoxy, alkoxyalkoxy, alkylthio, cyano, nitro, amino, hydroxy, alkylcarbonyl and alkoxycarbonyl groups. Alkyl, alkenyl, alkynyl and alkoxy moieties preferably have up to 6, more preferably up to 4, carbon atoms.

Preferably R represents a hydrogen atom or a group of formula $-(CO)_n(Y)_mR^2$ in which n is 0, Y is oxygen, m is 0 or 1 and $R^2$ represents a $C_{1-4}$ alkyl group. Most preferably R represents a hydrogen atom.

Preferably $R^1$ represents a phenyl group substituted by a halogen atom such as a fluorine, chlorine or bromine atom. The halogen atom may be located, for example, at the 4-position in the phenyl group.

It will be appreciated that the compounds of formula (I) may exist in different geometrically isomeric forms. The invention includes both individual isomers and mixtures of isomers.

The invention also includes a process for the preparation of compounds of formula (I), which comprises (A) reacting a compound of general formula:

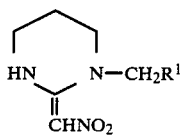 (II)

with a compound of general formula:

in which R and $R^1$ have the meanings given for the general formula (I) and L represents a leaving atom or group, in the presence of a base, or (B) reacting a compound of general formula $$RCONH(CH_2)_3NHCH_2R^1 \qquad (IV)$$

with a compound of general formula:

$$(Hal)_2C=CHNO_2 \qquad (V)$$

in which R and $R^1$ have the meanings given for the general formula (I) and Hal represents a halogen atom, in the presence of a base.

In the process (A) according to the invention, the leaving atom or group represented by L in formula (III) may be, for example, a halogen atom such as a chlorine atom, or an acyloxy group such as the group $R^3COO$ where $R^3$ is as defined for R. Conveniently, where a compound of formula (I) in which R represents a hydrogen atom is desired, a compound of formula (III) in which R represents a hydrogen atom and L represents a $C_{2-8}$ alkanoyloxy group, e.g. acetoxy, is employed.

The base may be an organic base such as a tertiary amine, e.g. a trialkylamine such as triethylamine, or an inorganic base such as an alkali metal hydroxide, e.g. sodium hydroxide; an alkali metal hydride, e.g. sodium hydride; an alkali metal carbonate, e.g. sodium carbonate; or an alkali metal alkoxide, e.g. potassium butoxide. The reaction is conveniently effected at a temperature in the range of $-50°$ to $50°$ C. Suitable solvents for the reaction include organic solvents such as chlorinated hydrocarbons, e.g. dichloromethane; amides, e.g. dimethylformamide; ethers e.g. tetrahydrofuran; and sulphoxides, e.g. dimethylsulphoxide.

In the process (B) according to the invention, the atom represented by Hal in general formula (V) may be, for example, a chlorine atom.

The reaction is conveniently effected at a temperature in the range of $-20°$ to $100°$ C. Suitable solvents for the reaction include halogenated hydrocarbons, e.g. dichloromethane, chloroform and carbon tetrachloride; hydrocarbons e.g. benzene or toluene; alcohols, e.g. t-butanol; ethers, e.g. dioxan or tetrahydrofuran; nitriles, e.g. acetonitrile; amides, e.g. dimethylformamide; sulphoxides e.g. dimethylsulphoxide; and mixtures thereof.

The base may be, for example, an inorganic base such as an alkali metal hydride, e.g. sodium hydride; an alkali metal hydroxide, e.g. sodium hydroxide; or alkali metal alkoxide, e.g. potassium alkoxide.

The compounds of general formula (IV) may be prepared by reacting a compound of general formula:

in which $R^1$ has the meaning given for the general formula I, with a compound of general formula (III) according to the method of the process (A), optionally in the absence of a base.

The compounds of general formula (II) may be prepared by the same or an analogous method to that described in EP-A-136636 referred to above.

The compounds of formula (VI) may be prepared, for example, by reacting propane 1,3-diamine with the appropriately substituted benzyl halide.

As mentioned above, the compounds of the invention are of interest as pesticides particularly against insect pests, for example aphids (genus Aphis); rice plant hoppers (genus Niloparvata) and rice leaf hoppers (genus Nephotettix). They are therefore particularly useful for combating pests found in rice crops.

Accordingly the invention includes pesticidal compositions comprising at least one carrier and, as active ingredient, a compound of the invention.

Such a composition may contain a single compound or a mixture of several compounds of the invention. It is also envisaged that different isomers or mixtures of isomers may have different levels or spectra of activity and thus compositions may comprise individual isomers or mixtures of isomers. The invention further provides a method of combating pests, particularly insect pests at a locus, which comprises applying to the locus a pesticidally effective amount of a compound or composition according to the present invention. An especially preferred locus is a paddy field bearing rice crops.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

A composition of the invention may also contain other ingredients, for example, one or more other compounds possessing pesticidal, herbicidal or fungicidal properties, or attractants, for example pheromones or food ingredients, for use in baits and trap formulations.

The following examples illustrate the invention.

EXAMPLE 1

Preparation of 1-formyl-3-(4-chlorobenzyl)-2-nitromethylene-hexahydropyrimidine 1-(4-Chlorobenzyl)-2-nitromethylene-hexahydropyrimidine (3 g) was added to a stirred suspension of sodium hydride (0.54 g) in dry dimethylformamide (150 ml) at room temperature under nitrogen and the stirring was continued overnight. Formic acetic anhydride (100% excess) was then added dropwise to the stirred suspension at 0°. The reaction mixture was then stirred for 1 hour. It was then poured onto water and extracted with dichloromethane (2×200 ml). The combined organic layers were dried (sodium sulphate) and the solvent removed in vacuo, to leave a solid. The solid was triturated with chloroform (5 ml) and was then filtered off, washed with chloroform (5 ml) and dried to afford the title compound (1.2 g), m.pt. 131°–133° C.

| Analysis | C | H | N |
|---|---|---|---|
| $C_{13}H_{14}N_3O_3Cl$ Requires: | 52.8 | 4.8 | 14.2 |
| Found: | 52.2 | 4.8 | 14.2 |

EXAMPLE 2

Determination of Toxicity Index

The toxicities of compounds relative to a standard insecticide, Parathion, against rice brown plant hoppers (*Nilaparvata lugens*) were tested by spraying 5 rice seedlings with aqueous dilutions of an acetone solution of test compound containing an emulsifier. Immediately after spraying, 10 adult hoppers were transferred to the seedlings and held for 48 hours, at which time the dead hoppers were counted. The tests were conducted employing several different dosage rates for each test compound.

In each instance, the toxicity of the compounds was compared to that of a standard pesticide, Parathion, the relative toxicity then being expressed in terms of the relationship between the amount of compound and the amount of the standard pesticide required to produce 50% mortality of the test insect. The standard pesticide is given an arbitrary Toxicity Index of 100. Thus a test compound having a Toxicity Index of 200 would be twice as active as the standard pesticide. The Toxicity Indices measured are given in the Table.

The following compounds were tested:

Test Compound A

1-Formyl-3-(4-chlorobenzyl)-2-nitromethylene-hexahydropyrimidine.

Test Compound B (Comparison Compound)

1-(4-Chlorobenzyl-2-nitromethylene-hexahydropyrimidine (corresponding to the product of Example 1 in EP-A-136636 referred to above).

TABLE

| Test Compound | Toxicity Index relative to Parathion = 100 |
|---|---|
| A | 520 |
| B | 340 |

Test compound A according to the invention is clearly much more active than the comparison compound against the rice pest *Nilaparvata lugens*.

We claim:

1. A 2-nitrohexahydropyrimidine compound of the formula:

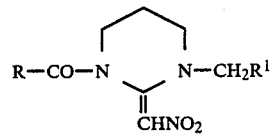

in which

R represents a hydrogen atom, a cycloalkyl group of 3 to 6 carbons, a cycloalkyl group of 3 to 6 carbons substituted with alkyl of 1 to 6 carbons or halogen, or a group of the formula $-(CO)_n(Y)_mR^2$;

n is 0 or 1;

Y is oxygen or sulfur;

m is 0 or 1;

$R^2$ is alkyl of 1 to 6 carbons; alkyl of 1 to 6 carbons substituted with halogen, alkoxy of 1 to 6 carbons, haloalkoxy of 1 to 6 carbons, alkoxyalkoxy of 2 to 6 carbons, hydroxy, alkanoyloxy of 1 to 6 carbons, thiol, cycloalkyl of 3 to 6 carbons, cycloalkyl of 3 to 6 carbons substituted with alkyl of 1 to 6 carbons or halogen, phenyl, or phenyl substituted with halogen, alkyl of 1 to 6 carbons, alkoxy of 1 to 6 carbons, haloalkyl of 1 to 6 carbons, haloalkoxy of 1 to 6 carbons, alkoxyalkoxy of 2 to 6 carbons, alkylthio of 2 to 6 carbons, CN, $NO_2$, $NH_2$, OH, alkylcarbonyl of 2 to 6 carbons, or alkoxycarbonyl of 2 to 6 carbons; alkenyl of 2 to 6 carbons; alkenyl of 2 to 6 carbons substituted with halogen, alkoxy of 1 to 6 carbons, haloalkoxy of 1 to 6 carbons, alkoxyalkoxy of 2 to 6 carbons, hydroxy, alkanoyloxy of 1 to 6 carbons, thiol, cycloalkyl of 3 to 6 carbons, cycloalkyl of 3 to 6 carbons substituted with alkyl of 1 to 6 carbons or halogen, phenyl, or phenyl substituted with halogen, alkyl of 1 to 6 carbons, alkoxy of 1 to 6 carbons, haloalkyl of 1 to 6 carbons, haloalkoxy of 1 to 6 carbons, alkoxyalkoxy of 2 to 6 carbons, alkylthio of 2 to 6 carbons, CN, $NO_2$, $NH_2$, OH, alkylcarbonyl of 2 to 6 carbons, or alkoxycarbonyl of 2 to 6 carbons; alkynyl of 2 to 6 carbons; or alkynyl of 2 to 6 carbons substituted with halogen, alkoxy of 1 to 6 carbons, haloalkoxy of 1 to 6 carbons, alkoxyalkoxy of 2 to 6 carbons, hydroxy, alkanoyloxy of 1 to 6 carbons, thiol, cycloalkyl of 3 to 6 carbons, cycloalkyl of 3 to 6 carbons substituted with alkyl of 1 to 6 carbons or halogen, phenyl, or phenyl substituted with halogen, alkyl of 1 to 6 carbons, alkoxy of 1 to 6 carbons, haloalkyl of 1 to 6 carbons, haloalkoxy of 1 to 6 carbons, alkoxyalkoxy of 2 to 6 carbons, alkylthio of 2 to 6 carbons, CN, $NO_2$, $NH_2$, OH, alkylcarbonyl of 2 to 6 carbons, or alkoxycarbonyl of 2 to 6 carbons; and $R_1$ is phenyl or phenyl substituted with halogen, alkyl of 1 to 6 carbons, alkoxy of 1 to 6 carbons, haloalkyl of 1 to 6 carbons, haloalkoxy of 1 to 6 carbons, alkoxyalkoxy of 2 to 6 carbons, alkylthio of 2 to 6 carbons, CN, $NO_2$, $NH_2$, OH, alkylcarbonyl of 2 to 6 carbons, or alkoxycarbonyl of 2 to 6 carbons.

2. A compound as claimed in claim 1 in which R represents a hydrogen atom or a group of formula $-(CO)_n(Y)_mR^2$ in which n is 0, Y is oxygen, m is 0 or 1, and $R^2$ represents a $C_{1-4}$ alkyl group.

3. A compound according to claim 2 wherein R is hydrogen.

4. A compound according to claim 3 wherein $R_1$ is phenyl or phenyl substituted with halogen, alkyl of 1 to 4 carbons, alkoxy of 1 to 4 carbons, haloalkyl of 1 to 4 carbons, haloalkoxy of 1 to 4 carbons, alkoxyalkoxy of 2 to 4 carbons, alkylthio of 2 to 4 carbons, CN, $NO_2$, $NH_2$, OH, alkylcarbonyl of 2 to 4 carbons, or alkoxycarbonyl of 2 to 4 carbons.

5. A compound according to claim 4 wherein $R^1$ represents a phenyl group substituted by a halogen atom.

6. A compound according to claim 5 wherein $R^1$ represents a phenyl group substituted at the 4-position by a halogen atom.

7. 1-Formyl-3-(4-chlorobenzyl)-2-nitromethylene-hexahydropyrimidine.

8. A pesticidal composition comprising at least one carrier and, as active ingredient, a pesticidally effective amount of a compound of claim 1.

9. A composition as claimed in claim 8, which comprises at least two carriers, at least one of which is a surface active agent.

10. A method of combating pests at a locus, which comprises applying to the locus a pesticidally effective amount of a compound of claim 1.

* * * * *